US006665558B2

(12) United States Patent
Kalgren et al.

(10) Patent No.: US 6,665,558 B2
(45) Date of Patent: Dec. 16, 2003

(54) SYSTEM AND METHOD FOR CORRELATION OF PATIENT HEALTH INFORMATION AND IMPLANT DEVICE DATA

(75) Inventors: James Kalgren, Lino Lakes, MN (US); Rene H. Wentkowski, White Bear Lake, MN (US); Jeffrey E. Stahmann, Ramsey, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 276 days.

(21) Appl. No.: 09/738,869

(22) Filed: Dec. 15, 2000

(65) Prior Publication Data

US 2002/0077562 A1 Jun. 20, 2002

(51) Int. Cl.$^7$ .............................................. A61B 5/045

(52) U.S. Cl. .......................... 600/510; 607/30; 607/31; 607/59

(58) Field of Search .......................... 600/510; 607/30, 607/31, 59

(56) References Cited

U.S. PATENT DOCUMENTS

| 4,316,249 | A | 2/1982 | Gallant et al. ............... 364/417 |
|---|---|---|---|
| 4,549,552 | A | 10/1985 | Groch et al. ................. 128/700 |
| 4,809,697 | A | 3/1989 | Causey, III et al. ... 128/419 PT |
| 4,825,869 | A | 5/1989 | Sasmor et al. .......... 128/419 PT |
| 4,964,410 | A | 10/1990 | Leahey et al. ............... 128/696 |
| 5,217,021 | A | 6/1993 | Steinhaus et al. ........... 128/702 |
| 5,311,874 | A | 5/1994 | Baumann et al. ........... 128/705 |
| 5,487,755 | A | 1/1996 | Snell et al. .................... 607/27 |
| 5,507,786 | A | 4/1996 | Morgan et al. ................ 607/27 |
| 5,513,645 | A | 5/1996 | Jacobson et al. ............ 128/710 |
| 5,549,654 | A | 8/1996 | Powell .......................... 607/32 |
| 5,578,063 | A | 11/1996 | Bocek et al. .................... 607/5 |
| 5,603,331 | A | * 2/1997 | Heemels et al. ............. 128/696 |
| 5,722,999 | A | 3/1998 | Snell ............................. 607/32 |
| 5,891,178 | A | 4/1999 | Mann et al. ................... 607/27 |
| 5,974,341 | A | 10/1999 | Er et al. ........................ 607/31 |
| 5,978,707 | A | 11/1999 | Krig et al. ..................... 607/14 |
| 6,016,442 | A | 1/2000 | Hsu et al. .................... 600/518 |
| 6,016,446 | A | 1/2000 | Belalcazar .................... 607/13 |

(List continued on next page.)

FOREIGN PATENT DOCUMENTS

| EP | 0565084 | 10/1993 | ......... A61B/5/0452 |
|---|---|---|---|
| EP | 0711531 | 5/1996 | ......... A61B/5/0452 |

OTHER PUBLICATIONS

Conley, V.L., et al., "Arrhythmia Display", United States Co–Pending Patent Application, SLWK Attorney Docket No. 279.217US1, pp. 1–30, (Filed Aug. 24, 1999).

Hiebert, J.F., et al., "Event Marker Alignment by Inclusion of Event Marker Transmission Latency in the Real–Time Data Stream", United States Patent Co–Pending Application, SLWK Attorney Docket No. 279. 216US1, pp. 1–28, (Filed Aug. 22, 1999).

Stahmann, J.E., et al., "System and Method for Displaying Cardiac Events", United States Co–Pending Patent Application, SLWK Attorney Docket No. 279.327US1, pp. 1–48, (Filed Dec. 15, 2000).

*Primary Examiner*—Hieu T. Vo
*Assistant Examiner*—Johnny H. Hoang
(74) *Attorney, Agent, or Firm*—Schwegman, Lundberg, Woessner & Kluth, P.A.

(57) ABSTRACT

A system and method for correlating health related data for display. The system includes a medical device recording data and a display producing device which correlates the data and simultaneously displays different types of data or displays two sets of the same type of data along with the circumstances at which the two sets of data were recorded. Such displays aid a physician in prescribing and ascertaining the efficacy of cardiac therapies.

26 Claims, 9 Drawing Sheets

U.S. PATENT DOCUMENTS

| | | | |
|---|---|---|---|
| 6,067,471 A | 5/2000 | Warren | 607/5 |
| 6,076,015 A | 6/2000 | Hartley et al. | 607/20 |
| 6,091,990 A | 7/2000 | Hsu et al. | 607/5 |
| 6,108,577 A | 8/2000 | Benser | 600/517 |
| 6,112,117 A | 8/2000 | KenKnight et al. | 607/5 |
| 6,308,095 B1 | 10/2001 | Hsu et al. | 600/518 |
| 6,312,378 B1 | 11/2001 | Bardy | 600/300 |
| 6,459,929 B1 * | 10/2002 | Hopper et al. | 600/513 |
| 6,459,934 B1 * | 10/2002 | Kadhiresan | 607/9 |

* cited by examiner

SYSTEM AND METHOD FOR CORRELATION OF PATIENT HEALTH INFORMATION AND IMPLANT DEVICE DATA

FIELD OF THE INVENTION

This invention pertains to a system and method of correlating general patient health information and implant device data, and more particularly for correlating patient health information and cardiac rhythm management device data.

BACKGROUND

Implantable cardiac rhythm management devices ("CRM devices") are well established therapeutic devices for treating patients who have experienced one or more documented episodes of hemodynamically significant ventricular tachycardia, ventricular fibrillation, bradycardia, or heart failure. Since their clinical inception more than two decades ago, CRM devices have evolved from basic to sophisticated electronic devices that provide physicians with a variety of clinically useful functions with which to treat patients.

Presently, even the most basic of CRM device typically has more than one tachycardia detection criterion, tiered therapy which combines bradycardia support pacing with various antitachycardia pacing modes, low-energy cardioversion, defibrillation, and data logging capabilities. The data logging capabilities within CRM devices have become increasingly important, since the amount of data required for the CRM device operation increases proportionally with the increase in CRM functions. Efficiently processing this large amount of data has become possible with the incorporation of microprocessors and memory within the CRM device.

Once a CRM device has been implanted, the physician interacts with the CRM device through a clinical programmer. The clinical programmer establishes a communication link with the implanted CRM device. The communication link allows instructions to be sent to the electronic circuitry of the CRM device and clinical data regarding the occurrence and treatment of a patient's cardiac arrhythmias and the CRM device's operation to be sent from the electronic circuitry of the CRM device to the clinical programmer. The typical programmer is a microprocessor-based unit that creates a communication link between the implanted CRM device and the programmer, and a graphics display screen that presents a patient's recorded cardiac data and CRM system information to the physician.

As the number of differing health data recorded by CRM device increases with each new generation of CRM device and the number of general patient health data increases, manufacturers and clinicians alike are becoming more sensitive to the role that time-efficient data interpretation plays in the physician's diagnosis of the patient. As CRM devices become increasingly complex, the interpretation of recorded arrhythmic episodes, operation of the CRM device, and the effect of changing a patient's therapy can be a challenging and time-consuming task.

Therefore, a need exists for improved CRM system and programmer technology that facilitates and correlates the identification of relevant information regarding the patient's clinical status. There is a need in the art for a system that correlates multiple data sets and displays same to the physician.

SUMMARY OF THE INVENTION

The present invention is generally directed to a system and method for presenting data from the CRM device simultaneously with patient health data and/or other patient data. The data so presented provides a physician with a visual display of more than one data set and thus the correlation between the data. Such a display may aid the physician in diagnosing and treating a patient.

Accordingly, one embodiment provides a cardiac rhythm management system including a cardiac rhythm management device and a programmer, the programmer being adapted to receive data from the cardiac rhythm management device. The programmer is adapted to correlate a first data set and a second data set for display to a physician. The first data set may be continuous, asynchronous or periodic data. The second data set may be asynchronous, continuous, or periodic data.

In another embodiment of the invention, the data is downloaded from the programmer into a data processor, which correlates the data. The correlated data is then output to a display device. One example of a data processor is a computer running appropriate software. One example of the display device is a computer monitor.

A further embodiment provides a display of the reoccurring first data against time and a second data imposed on the time axis to indicate a change in the patient's therapy. The second data may include changes to a patient's therapy including medication changes, medical device changes, or changes in operational parameters of a medical device.

Another embodiment provides a graphical display of data of the same type, which were recorded under different conditions, for example at different times or when the patient was under different treatment. The different circumstances are also displayed.

In another embodiment, the same type of data is heart rate variability data and the different circumstances may be the time at which the heart rate variability data was measured.

These and other embodiments, aspects, advantages, and features of the present invention will be set forth in part in the description which follows, and in part will become apparent to those skilled in the art by reference to the following description of the invention and referenced drawings or by practice of the invention. The aspects, advantages, and features of the invention are realized and attained by means of the instrumentalities, procedures, and combinations particularly pointed out in the appended claims.

DESCRIPTION OF THE INVENTION

In the following detailed description of the invention, reference is made to the accompanying drawings which form a part hereof, and in which is shown, by way of illustration, specific embodiments in which the invention may be practiced. These embodiments are described in sufficient detail to enable those skilled in the art to practice the invention. Other embodiments may be utilized and structural, logical, and electrical changes may be made without departing from the scope of the present invention.

The embodiments of the present invention illustrated herein are described as being included in a cardiac rhythm management device, e.g. an implantable cardiac defibrillator, pacemaker, or heart failure treatment device, which may include numerous pacing modes known in the art, and an external medical device programmer. The medical system and method of the present invention could also be implemented in an external cardioverter/monitor system as are known in the art. The medical system and method of the present invention could also be implemented in an implantable atrial cardioverter-defibrillator, which may include numerous pacing modes known in the art. Furthermore, although the present invention is described in conjunction with an implantable defibrillator having a microprocessor based architecture, it will be understood that the implantable cardiac defibrillator (or other implanted device) may be implemented in any logic based, custom integrated circuit architecture, if desired.

Figure 1:
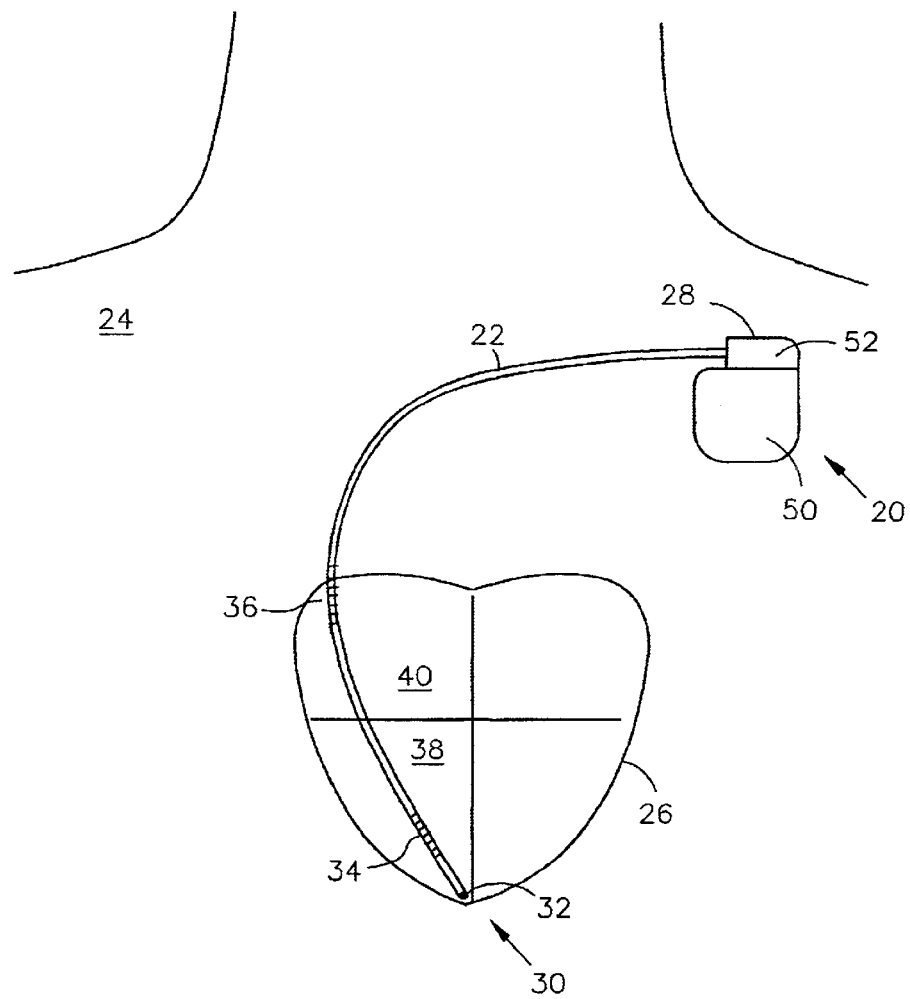
FIG. 1 is an embodiment of an implantable cardiac rhythm management device.

FIG. 1 shows one embodiment of a medical device system which includes a CRM device 20 electrically and physically coupled to at least one lead 22 such as an intracardiac catheter, epicardial lead, or coronary vein lead. In one embodiment, the intracardiac catheter 22 includes one or more pacing electrodes and one or more intracardiac defibrillation electrodes.

The intracardiac catheter 22 is implanted in a human body 24 with portions of the intracardiac catheter 22 inserted into a heart 26 or placed on the heart 26 to detect and analyze electric cardiac signals produced by the heart 26 and to provide electrical energy to the heart 26 under certain predetermined conditions to treat cardiac arrhythmias of the heart 26, including ventricular fibrillation, bradycardia and/or heart failure.

In one embodiment, the intracardiac catheter 22 is an endocardial lead adapted to be releasably attached to CRM device 20. The intracardiac catheter 22 has an elongate body with a proximal end 28 and a distal end 30 and is shown as having a pacing electrode 32 located at, or adjacent, the distal end 30 of intracardiac catheter 22. In one embodiment, the pacing electrode 32 is a tip electrode positioned at the distal end 30 of intracardiac catheter 22. Alternatively, pacing electrode 32 is an annular, or a semi-annular ring electrode positioned adjacent the distal end 30.

The intracardiac catheter 22 also includes one or more defibrillation electrodes. In one embodiment, the intracardiac catheter 22 has a first defibrillation electrode 34 and a second defibrillation electrode 36, where the first defibrillation electrode 34 and the second defibrillation electrode 36 are defibrillation coil electrodes. The first defibrillation electrode 34 is spaced apart and proximal to the pacing electrode 32, and the second defibrillation electrode 36 is spaced apart and proximal to the first defibrillation electrode 34 such that when the intracardiac catheter 22 is positioned within the heart 26, the pacing electrode 32 and first defibrillation electrode 34 reside within a right ventricle 38 of the heart 26, with pacing electrode 32 in an apex location within the right ventricle 38, and second defibrillation electrode 36 is positioned within the right atrium chamber 40 of heart 26 or a major vein leading to right atrium chamber 40 of heart 26. The description of catheter 22 is but one example of various leads, known to one of skill in the art, that will work with the present invention. As a further example CRM device 20 may be connected to a plurality of leads.

Figure 2:
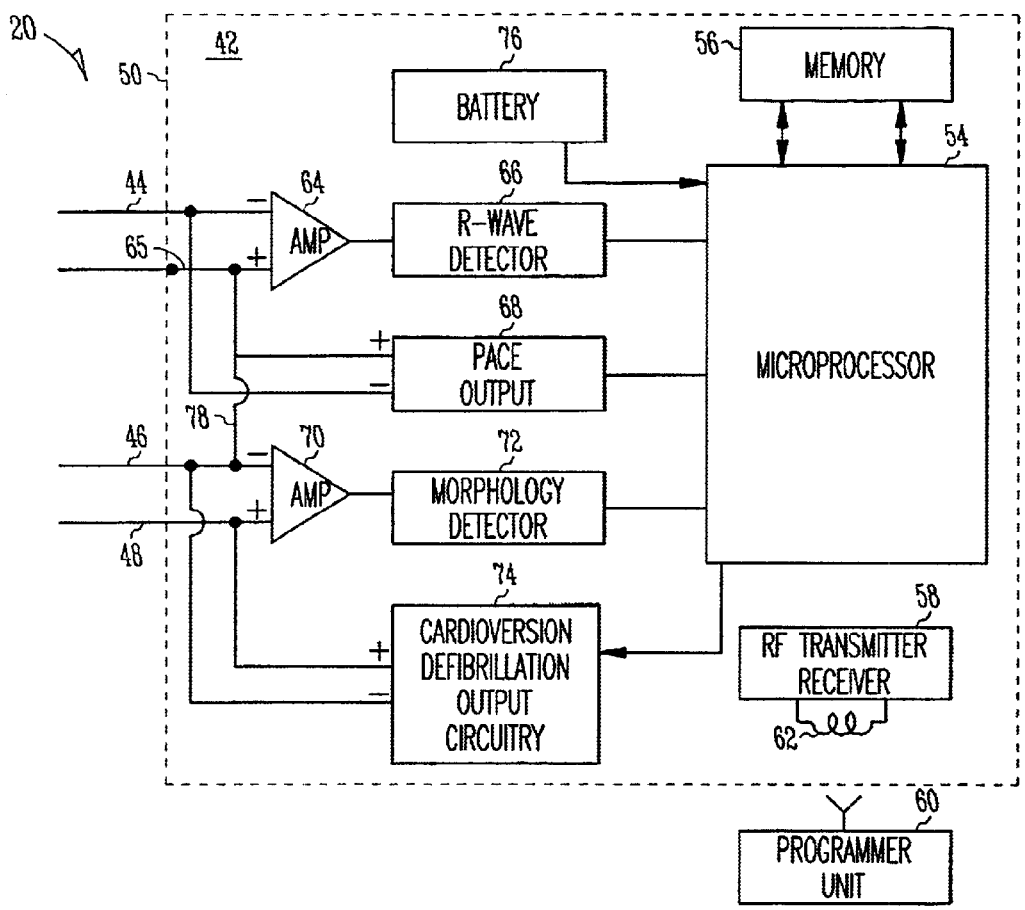
FIG. 2 is a block diagram of an implantable cardiac rhythm management device.

FIG. 2 shows an embodiment of a block diagram of CRM device 20. The CRM device 20 includes electronic control circuitry 42 for receiving cardiac signals from heart 26 and delivering electrical energy to heart 26. The electronic control circuitry 42 includes terminals, labeled with reference numbers 44, 46, and 48 for connection to electrodes attached to the surface of intracardiac catheter 22. Pacing electrode 32 is electrically connected to terminal 44 and to the electronic control circuitry 42 through an electrically insulated conductor provided within the elongate body of intracardiac catheter 22. The first defibrillation electrode 34 and the second defibrillation electrode 36 are connected to terminals 46 and 48, respectively, and to electronic control circuitry 42 through electrically insulated conductors provided within the elongate body of intracardiac catheter 22.

In one embodiment, electronic control circuitry 42 of CRM device 20 is encased and hermetically sealed in a housing 50 suitable for implanting in a human body. In one embodiment, titanium is used for the housing 50, however, other biocompatible housing materials as are known in the art may be used. A connector block 52 is additionally attached to the housing 50 of CRM device 20 to allow for the physical and the electrical attachment of the intracardiac catheter 22 and the electrodes to CRM device 20 and the encased electronic control circuitry 42 (FIG. 1).

Electronic control circuitry 42 is a programmable microprocessor-based system, with a microprocessor 54 and a memory circuit 56, which contains parameters for various pacing and sensing modes (FIG. 2). Memory circuit 56 stores data indicative of cardiac signals received by the electronic control circuitry 42. In one embodiment, data stored in the memory circuit 56 includes arrhythmia episode details, such as: a raw electrocardiogram signals, including two or more channels such as a ventricular signal and an atrial signal; a chronological number of the episode; the date and time of the episode; the type of episode detected; the onset rate of the episode; the stability of the episode; the duration of the episode; pre-therapy and post-therapy average atrial and ventricular rates; and the type of therapy delivered. Other arrhythmia episode data known in the art can also be recorded and stored in memory circuit 56. Moreover, the data stored in memory circuit 56 can include lead impedance measurements, pacing threshold measurements, brady pacing parameters, and programmed therapy parameters. The stored data may also include patient health data, for example, maximum heart rate, heart rate variability data, and blood pressure measurements.

Electronic control circuitry 42 further includes transmitter circuit 58 which is coupled to memory circuit 56 to allow the CRM device 20 to communicate with a programmer unit 60. In one embodiment, transmitter circuit 58 and programmer unit 60 use a wire loop antenna 62 and a radio frequency telemetric link to receive and transmit signals and data to and from the programmer unit 60 and the electronic control circuitry 42. In another embodiment, the transmitter circuit 58 includes inductive coils to bidirectionally transmit signals and data between programmer unit 60 and electronic control circuitry 42. In these manners, programming commands or instructions are transferred to the microprocessor 54 of CRM device 20 after implant, and stored cardiac data pertaining to patient health, including sensed arrhythmic episodes within the heart 26, and subsequent therapy, or therapies, applied to correct sensed arrhythmic events are transferred to programmer unit 60 from CRM device 20. It is within the scope of the present invention to transmit any data stored in CRM device 20 to programmer unit 60 so the data can be analyzed and used by a physician to diagnose and evaluate the efficacy of the therapy.

Pacing electrode 32 is coupled to a sense amplifier 64 through terminal 44 in the FIG. 2 embodiment. In an additional embodiment, the housing 50 of CRM device 20 is also coupled to the sense amplifier 64 at 65 to allow for unipolar cardiac rate sensing between the pacing electrode 32 and the housing 50 of CRM device 20. The output of the sense amplifier 64 is shown connected to an R-wave detector 66. These components serve to sense and amplify the QRS waves of the heart, and apply signals indicative thereof to the microprocessor 54. Among other things, microprocessor 54 responds to the R-wave detector 66 by providing pacing signals to a pace output circuit 68, as needed according to the programmed pacing mode. Pace output circuit 68 provides output pacing signals to terminals 44 and 46, which connect to the pacing electrode 32 and defibrillation electrode 34, for cardiac pacing. As illustrated in FIG. 2, the pace output circuit is also connected to housing 50 at terminal 65 and through connection 78 to terminal 46. In another embodiment, the connection to defibrillation electrode 34 is accomplished by intracardiac catheter 22 instead of CRM device 20. As will be appreciated by one of skill in the art, this is one of many structures for sensing cardiac rates and production of cardiac rhythm management signals.

First defibrillation electrode 34 and second defibrillation electrode 36 are coupled to a sense amplifier 70, whose output is connected to a cardiac morphology detector 72. These components serve to sense and amplify the QRS-waves of the cardiac cycle from the ventricular region of the heart 26, and apply signals indicative thereof to the microprocessor 54. In one embodiment, the cardiac morphology detector 72 includes an analog filter for filtering cardiac signal noise sensed by the electrodes. The cardiac signals are then band limited before arriving at an analog-to-digital filter. The cardiac signals are then A/D converted into a digital signal and subsequently received by microprocessor 54. In an alternative embodiment, the cardiac signals are filtered through an analog peak detector to extract the maximum and minimum cardiac signal values for each sensed cardiac interval.

Microprocessor 54 responds to the cardiac signals sensed within the heart 26 using the intracardiac catheter 22 by providing signals to cardioversion/defibrillation output circuitry 74 to provide either cardioversion or defibrillation electrical energy to the heart 26 depending upon nature of an arrhythmia sensed by CRM device 20. Power to CRM device 20 is supplied by an electrochemical battery 76 that is housed within CRM device 20.

While the illustrative embodiment show in FIG. 2 has R-Wave detector 66 and morphology detector 72, it is understood that one or the other of these detectors could be removed from the CRM device 20. Moreover, other detectors could be installed in CRM device 20 to monitor various health data of a patient.

Figure 3:
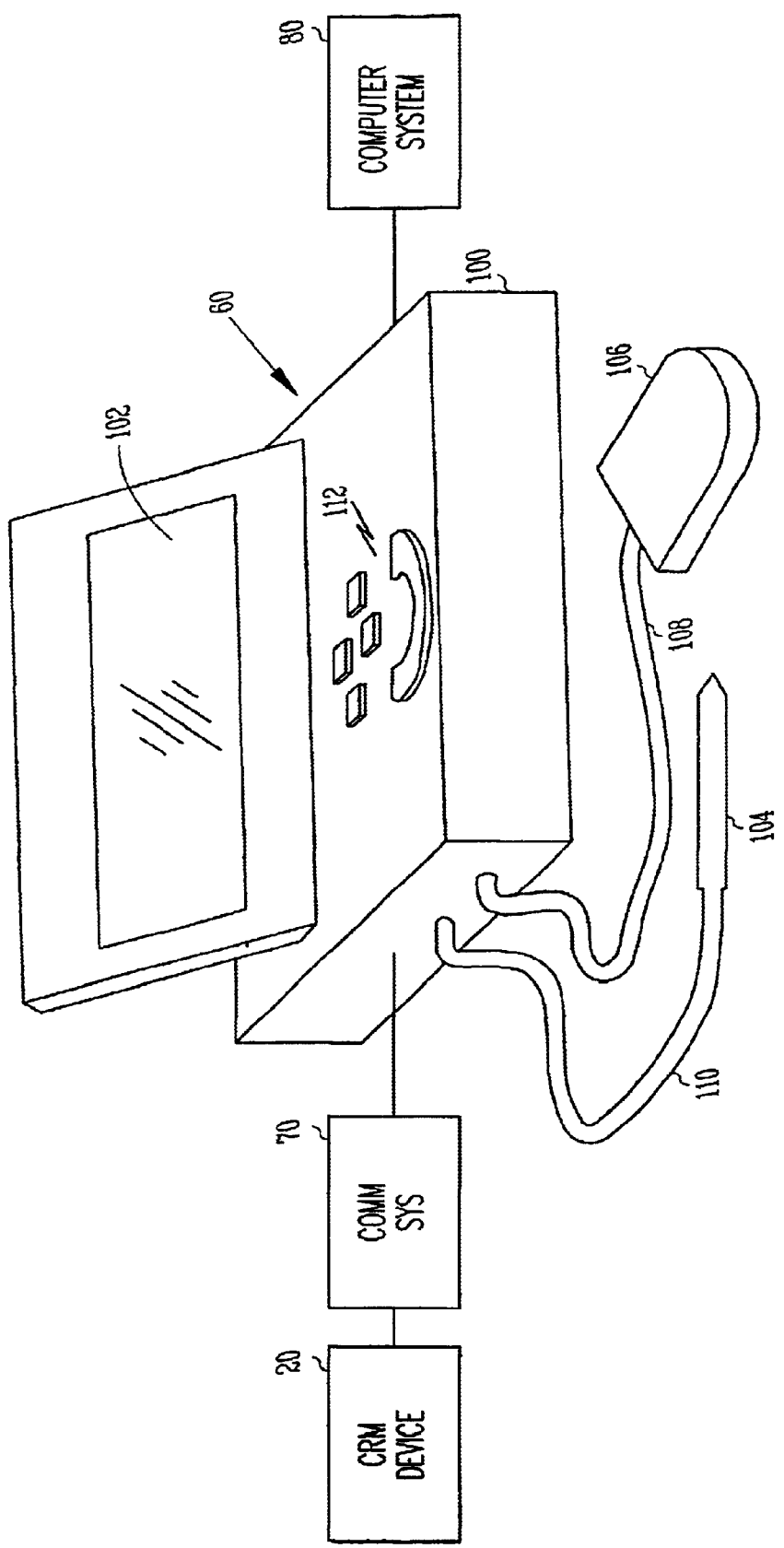
FIG. 3 is a perspective view of a programmer unit and computer system.

Referring now to FIG. 3, there is shown one embodiment of a medical device programmer 60 of the medical device system. As previously mentioned, one embodiment of the medical device programmer 60 for the implantable CRM device 20 takes the form of an external controller. However, in an alternative embodiment, the medical device system is a completely external device such as an external cardioverting/defibrillator system as are known in the art, where the programmer unit is physically and electronically integrated into electronic control circuitry similar to the electronic control circuitry 42 of CRM device 20. An example of this latter embodiment is for an external cardiac monitor and defibrillation unit, electrically connected to the heart by any combination of intracardiac catheters, epicardial electrodes and/or external cardiac electrodes.

Medical device programmer 60 is designed to be positioned external of the human body 24 for communicating with an implantable medical device, such as CRM device 20 from FIG. 1, for example via RF telemetry. Medical device programmer 60 has programmer electronic circuitry, including a microprocessor and related circuitry, such as digital memory, which is coupled to an output unit, which is here shown as graphics display screen 102.

In one embodiment, the medical device programmer 60 comprises an outer housing 100 which is made of a thermal plastic or other suitable lightweight durable material. The graphics display screen 102 is disposed on the upper surface of housing 100. The graphics display screen 102 folds down into a closed position when medical device programmer 60 is not in use, thereby reducing the size of medical device programmer 60 and protecting the display surface of graphics display screen 102 during transportation and storage. In an additional embodiment, the external programmer additionally has a floppy disk drive and a hard drive disposed within the housing.

The medical device programmer 60 is shown with the graphics display screen 102 positioned in one of a plurality of possible open positions such that a display on the graphics display screen 102 is visible to a user situated in front of medical device programmer 60. In one embodiment, the graphics display screen 102 is of a CRT, LCD or electroluminescent type. The graphics display screen 102 is operatively coupled to the electronic circuitry disposed with the housing 100 and is adapted to provide a visual display of graphics and/or data under control of the programmer electronic circuitry, e.g. processor. It is within the scope of the present invention to provide programmer 60 with a video output connection to which a non-integral monitor can be connected.

Medical device programmer 60 further includes a user input device coupled to the electronic circuitry. In one embodiment, the user input device is the graphics display screen 102, which is provided with touch-sensitive capability, such that a user can interact with the programmer electronic circuitry by touching the display area on the graphics display screen 102 with a finger (not shown) or a stylus 104. In one embodiment, the touch-sensitive graphics display screen is primary input for the medical device programmer 60. The medical device programmer 60 further includes a programming head 106, which is place over a patient's body near the implant site of an implanted device, such as CRM device 20, in order to establish a communication link between CRM device 20 and programmer 60.

The telemetry link between CRM device 20 and programmer 60 allows the electronic circuitry of programmer 60 to be coupled to the electronic control circuitry of the CRM device 20. The programming head 106 is coupled to the electronic circuitry of medical device programmer 60 and a receiver circuit for receiving signals from the transmitter circuit indicative of cardiac signals by a cable 108. In one embodiment, a communication system 70 is intermediate programmer 60 and CRM device 20, for example the telephone system or a computer network such as a LAN, WAN, or global computer network (e.g. internet). Consequently, the programmer 60 remotely monitors and receives data from the CRM device 20.

In one embodiment of the invention, the stylus 104 used to interact with the touch-sensitive graphics display screen 102 is coupled to the programmer electronic circuitry within the housing 100 by a cable 110. In another embodiment of the invention, only a touch sensitive screen 102 is provided which is activated by a user's finger touching the screen. Alternatively, medical device programmer 60 may be equipped with a conventional computer "mouse"-type pointing device, rather than a stylus or a touch sensitive screen which is actuatable by a user's finger. In the absence of either a stylus, touch-sensitive screen or a mouse, on-screen cursor control for enabling user interaction with medical device programmer 60 may be facilitated through cursor control keys 112 (arrow keys or the like) disposed on medical device programmer 60.

Medical device programmer 60 further includes a receiver circuit for receiving signals from the transmitter circuit indicative of cardiac signals. Through the communication link with CRM device 20, the medical device programmer 60 is capable of capturing and storing recorded data transmitted from CRM device 20 and displaying the data on its graphics display screen 102. Programmer 60 compiles data into numerous forms for display on graphics display screen 102, such forms include charts and graphs, for example those shown in FIGS. 5–11. The programmer 60 may also include other forms of display and output devices such as printers and plotters. Moreover, programmer 60 can store the downloaded data and build a database containing the patient's therapy and health data, which can be downloaded to known computer readable media for long term storage.

In one embodiment, programmer 60 downloads the data it receives from CRM device 20 to a computer system 80 (FIG. 3) via a communication path. Computer system 80 includes memory for storing the downloaded data, a processor and associated software for correlating the data, and a display device for displaying the correlated data. Display devices include display screens, monitors, printer, plotters, etc. It will be understood that all the data correlating and data display functions described herein as being performed by programmer 60 are also performable by computer system 80, but for simplicity of explanation the following description refers to programmer 60.

While the above describes one embodiment of a medical system in which the present invention can be incorporated, it will be understood that the present invention can be incorporated into numerous CRM devices and programmers. Therefore, it will be understood by those of skill in the art that the present invention can be adapted for use with other types of CRM devices, examples of such devices are found in U.S. Pat. Nos. 6,112,117; 6,108,577; 6,091,990; 6,076,015; 6,067,471; 6,016,446; and 5,978,707, all assigned to the present assignee, and all herein incorporated in their entirety by reference. It will also be understood by those of skill in the art that the present invention can be adapted for use with other types of programmers.

Figure 4:
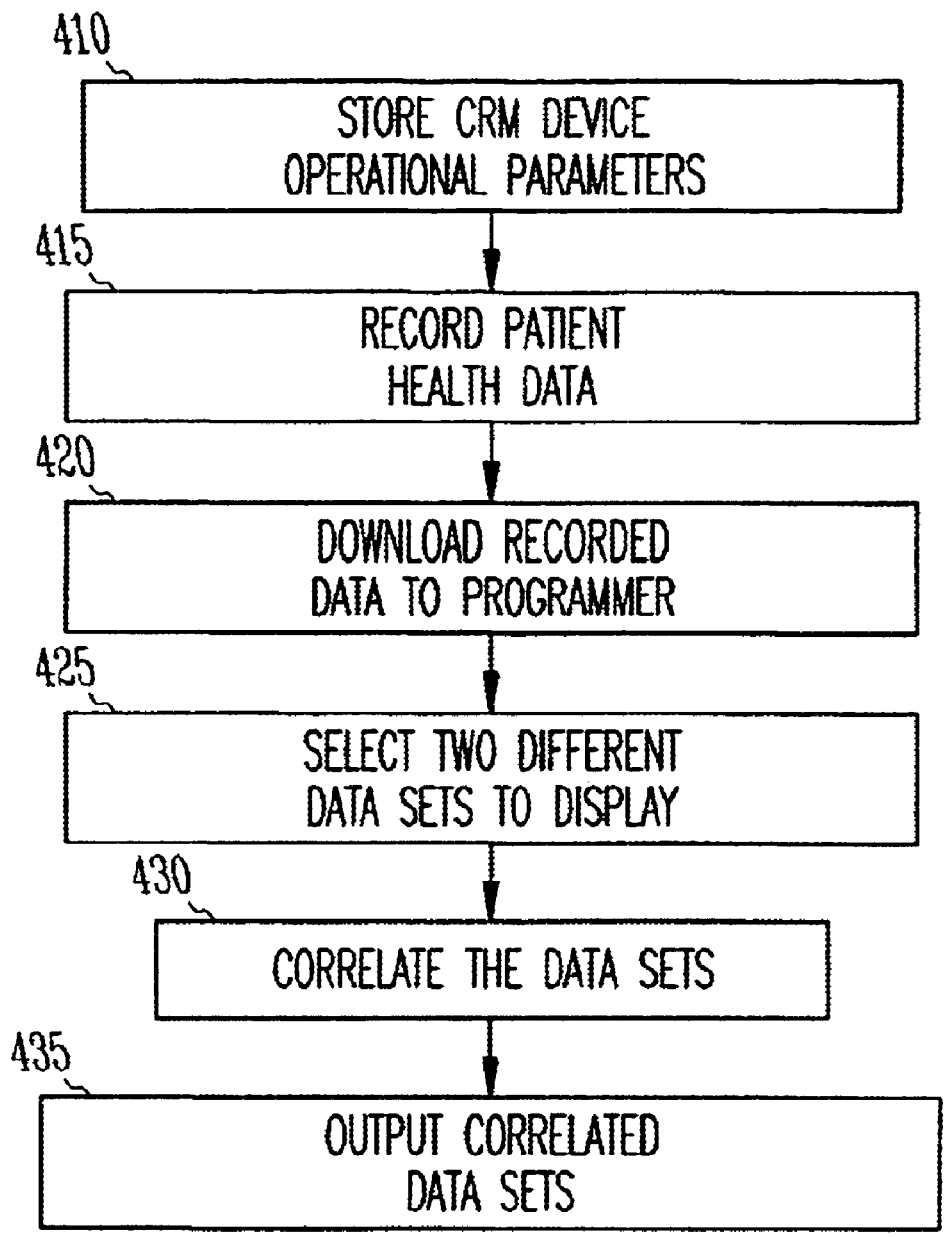
FIG. 4 is a flow chart of an embodiment of the present invention.

FIG. 4 shows a flow chart representing one embodiment of a process for producing and displaying two distinct sets of data. The CRM device programmable parameters are stored in CRM memory 56 (410), for example by the programmer 60 communicating the selected parameters via a communication link. CRM device 20 provides therapy to a patient and records various health data, for example tachy episodes, brady episodes, maximum heart rate, minimum heart rate, mean heart rates, heart rate variability, patient activity, blood pressure, etc. (415). The CRM device 20 also records its system parameters at the time it makes certain patient health measurements. In another embodiment of CRM device 20, it stores other therapy data, such as drug therapy data, which is not delivered or measured by CRM device 20. During a clinical visit by a physician, CRM device 20 downloads recorded data to the programmer 60 (420). At this time programmer 60 may include previously downloaded patient health data and CRM device parameters from previous patient therapies and add the newly downloaded information to a patient record stored in a database. The physician now selects two different sets of patient/CRM device data to display, for example on graphics display 102 of programmer 60 (425). The programmer 60 correlates the two different data sets (430). For example, if the two data sets are patient activity and a CRM device parameter change, then programmer 60 graphs patient activity before and after the CRM device parameter change. The programmer 60 displays the correlated data sets. Thus, a physician can readily visually comprehend the effect the data sets have on each other or a change in patient health. In the above example, the physician can visualize the effect the CRM device parameter change had on patient activity.

Figure 5:
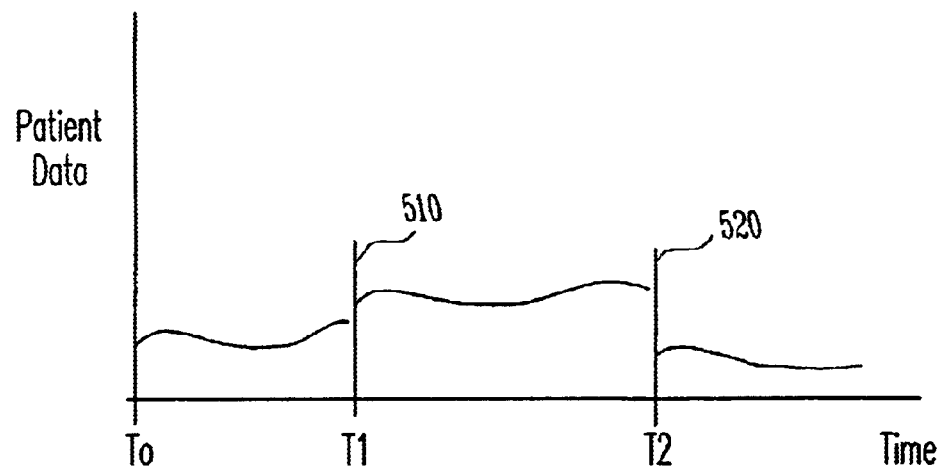
FIG. 5 is a graph of a patient's therapy history and further patient health/therapy data verses time according to one embodiment of the invention.

FIG. 5 shows an embodiment of a graph produced by programmer 60 and displayed on graphical display 102. The FIG. 5 graph displays selected patient health data represented on the Y-axis and time represented on the X-axis with selected asynchronous data superimposed on the graph. In an embodiment, the patient health data is periodically collected over time. In another embodiment, the data is continuous data. The selected patient health data for a time period between time $t_0$ and time $t_1$ is graphically displayed as shown in FIG. 5. At time $t_1$, an event 510 in the patient's therapy occurs and is graphically displayed. Here, the event is shown as a line but other representations are within the scope of the invention. This event can include, but is not limited to, changes in the CRM device parameters and patient's medications. In the area of the graph between time $t_1$ and time $t_2$, the selected patient health information is displayed which represents the patient health data after event 510. As a result of graphing both the patient health data and the event 510, the physician can quickly visualize the effect, if any, event 510 had on the patient health data by comparing the graphical display before the event (area between $t_0$ and $t_1$) with the graphical display after event (area between $t_1$ and $t_2$). In an embodiment, the event 510 can be labeled such that the physician will be informed upon viewing the display what the event 510 is. Such a label can be a indicia adjacent the line indicating event 510 or a legend outside the graph such that the data in the graph is not obscured.

FIG. 5 further shows that the present invention can include multiple events 510 and 520 on a single graph of the selected patient health data versus time. As a result, the area of the graph between time $t_1$ and time $t_2$ graphically displays the patient health data after first event 510 and before second event 520. The area of the graph after time $t_2$ graphically displays the patient health data after second event 520. The physician can now ascertain the effect the events 510 and 520 had on patient's health which is represented by the selected patient health data on the Y-axis. Events 510 and 520 can represent the same type of event, for example, changes in accelerometer response factor, lower rate limit, brady pacing parameters, etc. Events 510 and 520 can also represent two different type of events such the graph shows the effect on the patient health data of the first event 510 and the effect on the patient health data of the different, second event 520, such as a drug therapy change or a programmed parameter change in CRM device 20.

Figure 6:
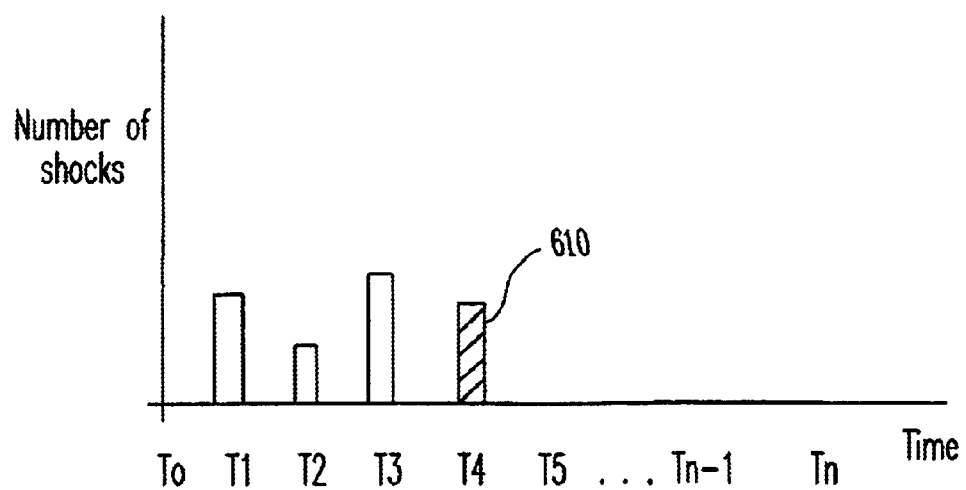
FIG. 6 is a graph of a patient's therapy history and change in ventricular sensitivity verses time according to one embodiment of the invention.

Specific examples of the graphs produced by the described embodiment of the system will now be described in conjunction with FIGS. 6–8. As discussed above, CRM device 20 records therapy history and numerous patient health data sets and downloads same to programmer 60. The recorded therapy history includes the number of electrical shocks administered by the CRM device to the patient's heart. The programmer, when instructed by the physician to do so, for example by touching display screen 102 with stylus 104, graphs the number of shocks delivered in discrete time periods ($t_1, t_2, t_3, \ldots t_n$), for example in a day, week, etc., versus time, for example, week, month, etc. (FIG. 6). In the displayed time period at time $t_4$, the ventricular sensitivity of CRM device 20 was changed. This change in ventricular sensitivity is represented by a cross hatched vertical bar 610 whereas the number of shocks administered at the time intervals are displayed in a different format, here non-crosshatched vertical bars. Moreover, the bar 610 represents that the change in ventricular sensitivity occurred during the time period in which the data represented thereby was recorded. Specifically, if bar 610 represents a weeks worth of data, then the ventricular sensitivity change occurred during that week As a result, the FIG. 6 graph shows the number of shocks administered by the CRM device over time $t_0$ to time $t_4$ at a first ventricular sensitivity and the number of shocks administered by the CRM device over time $t_4$ to time $t_n$ at a second ventricular sensitivity with a visual indicator showing when the change in ventricular sensitivity occurred.

In another embodiment, different representations of bar 60, for example different colors, hatching, etc., represent when the change in ventricular sensitivity occurred. In one embodiment, vertical hatching of bar 610 represents changing ventricular sensitivity (second data) after the number of shocks (first data) were recorded. In one embodiment, horizontal hatching of bar 610 represents changing ventricular sensitivity (second data) before the number of shocks (first data) were recorded. Accordingly, the physician can visualize the effect the change in ventricular sensitivity had on the number of shocks administered to the patient's heart. In the illustrated embodiment of FIG. 6, the effect the change in ventricular sensitivity 610 had was to reduce the number of shocks administered to zero. If additional shocks occurred, then the data bars, in one embodiment, occurring after time $t_4$ would also be cross hatched so that the displayed data readily indicates data that was recorded before and after a change in another data, here ventricular sensitivity. In another embodiment, the first data recorded before the event represented by the second data is displayed in a first color and the first data recorded after the event represented by the second data is shown in a second color.

Therapy history as stored in memory 56 of CRM device 20 and downloaded to programmer 60 further includes patient activity data and which chambers of the patient's heart required pacing at specific times. Patient activity data is a measurement of the percent of a fixed time period, e.g. a day, at which a patient reaches an activity threshold, e.g. time patient has a heart rate above a predetermined threshold value such as beats per minute threshold value. The programmer, when instructed by a physician to do so, displays a graph of the patient's activity versus time (FIG. 7). The physician has also instructed the programmer 60 to display the pacing chamber performance of CRM device 20. Here, the FIG. 7 graph shows the pacing chamber to be both ventricles (BV), right ventricle (RV), or left ventricle (LV). The physician can visualize the relationship of the patient's activity with the CRM device's pacing chamber activity.

Figure 7:
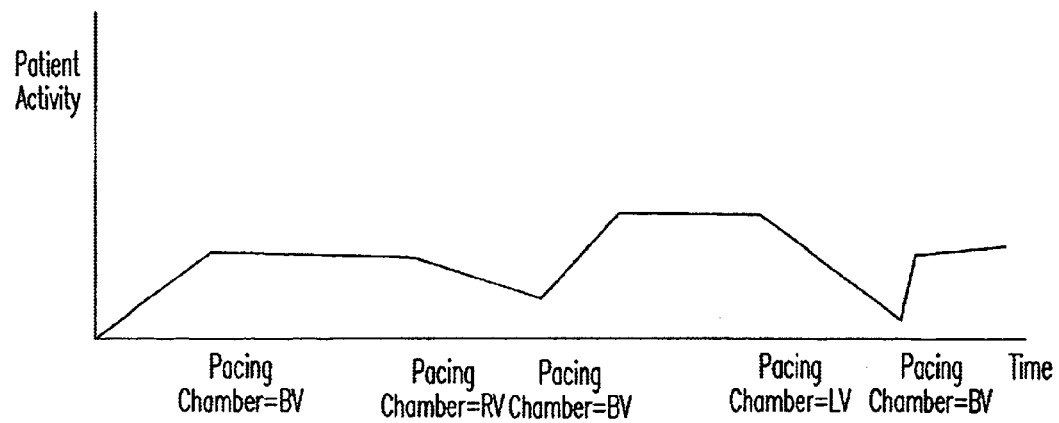
FIG. 7 is a graph of a patient's activity and pacing chamber versus time according to one embodiment of the invention.
Figure 8:
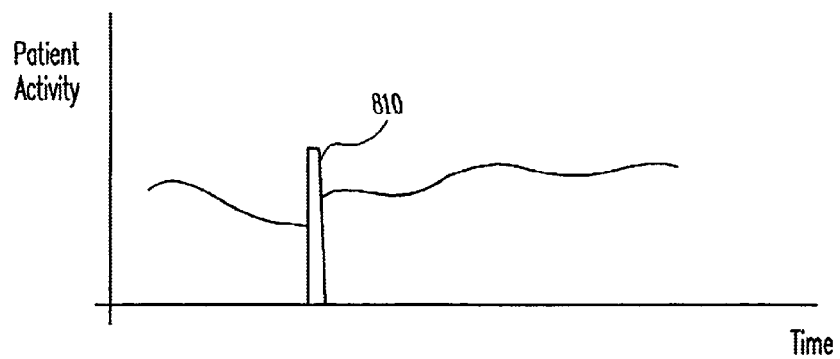
FIG. 8 is a graph of a patient's activity and change in accelerometer versus time according to one embodiment of the invention.

FIG. 8 shows a graph produced by programmer 60 which also displays patient activity versus time but unlike FIG. 7 the second data type displayed is when a change in accelerometer response factor occurred. The change in accelerometer response factor is indicated at 810 in FIG. 8 by a vertical bar. Accordingly, the physician can visualize the effect changing the accelerometer response factor had on the patient activity as measured by CRM device 20 by comparing the area of the graph to the left of bar 810 with the area of the graph to the right of bar 810.

Figure 9:
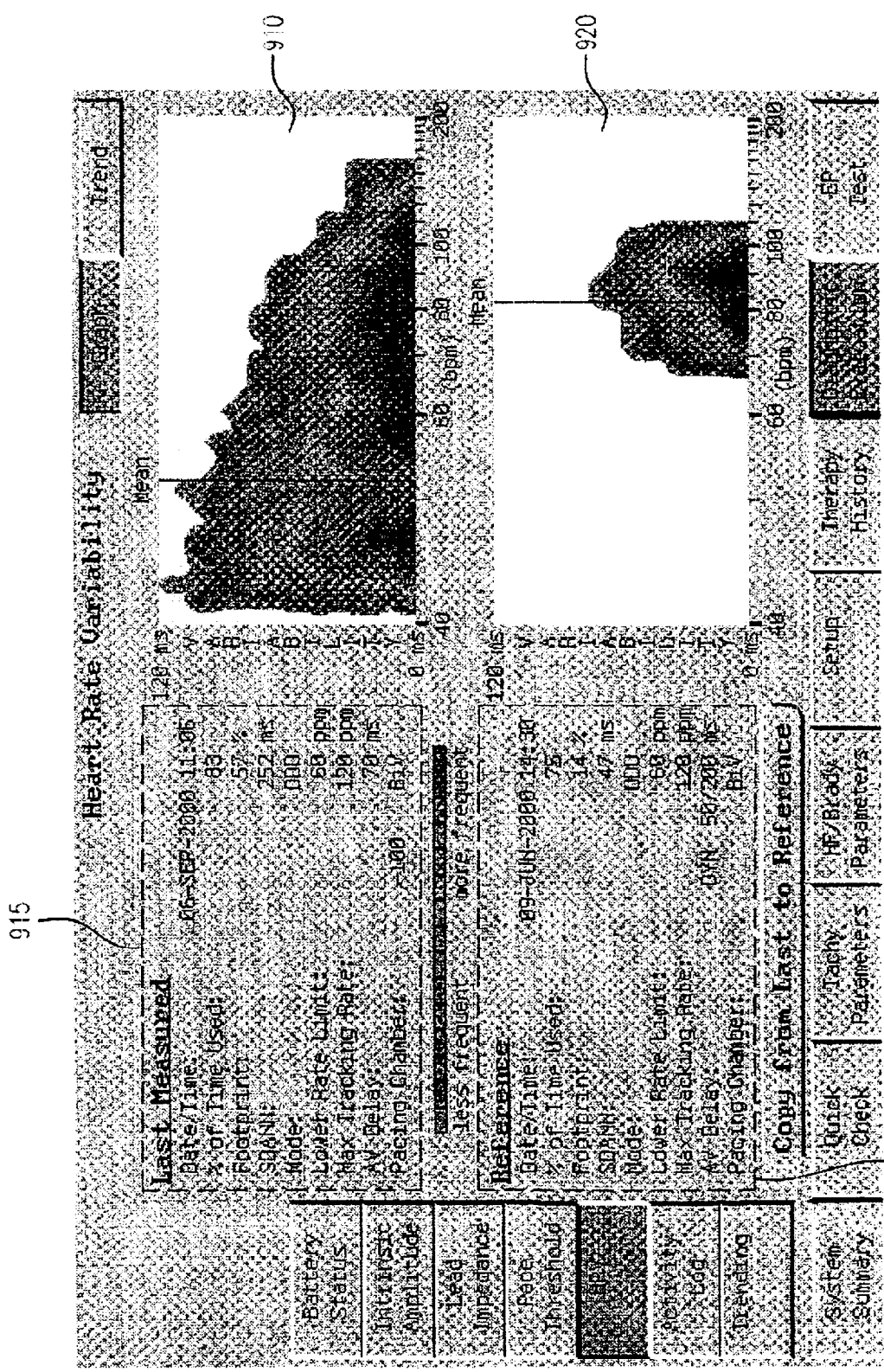
FIG. 9 is a display simultaneously showing two Heart Rate Variability graphs according to one embodiment of the invention.
Figure 10:
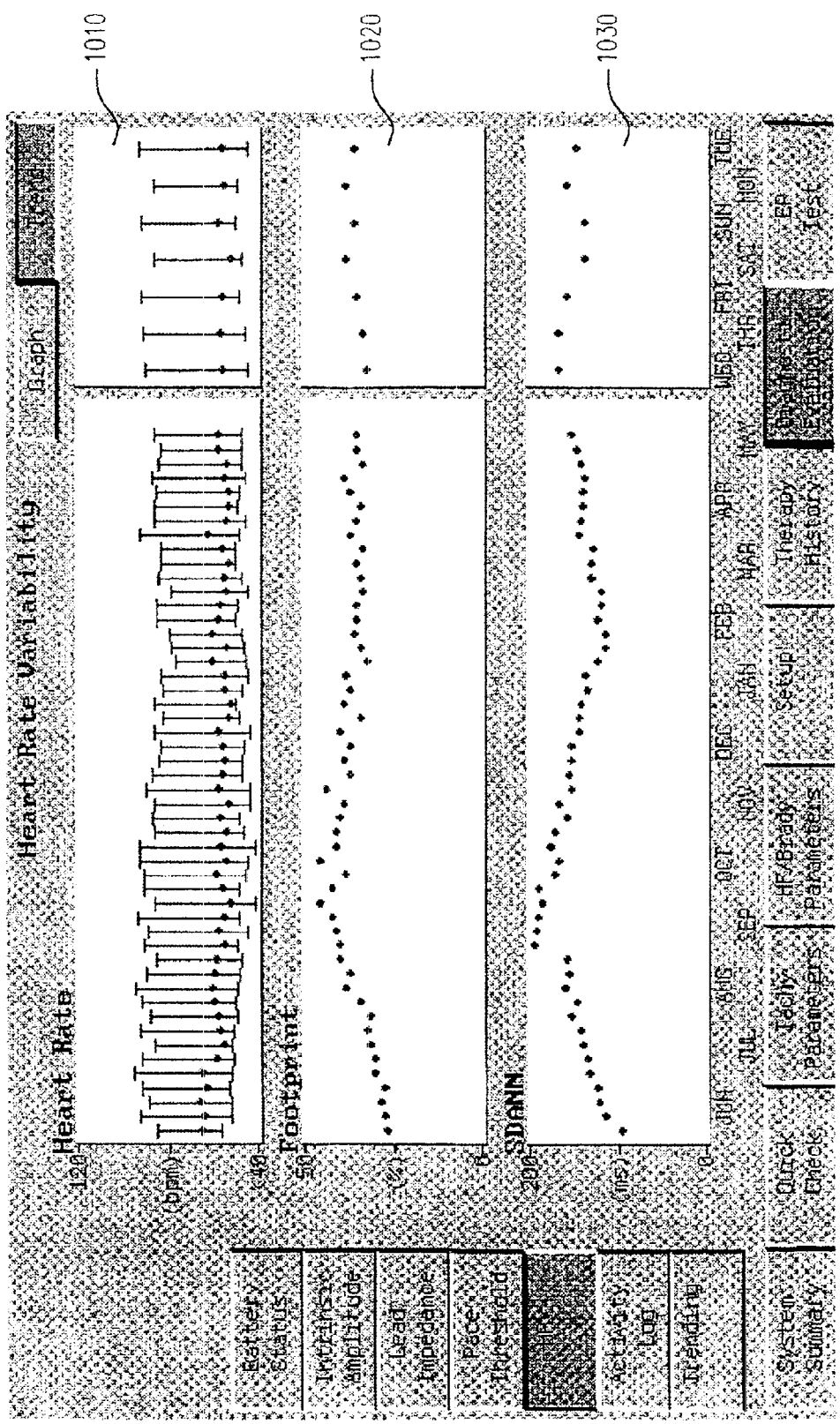
FIG. 10 is a display of trend data associated with Heart Rate Variability measurements according to one embodiment of the invention.
Figure 11:
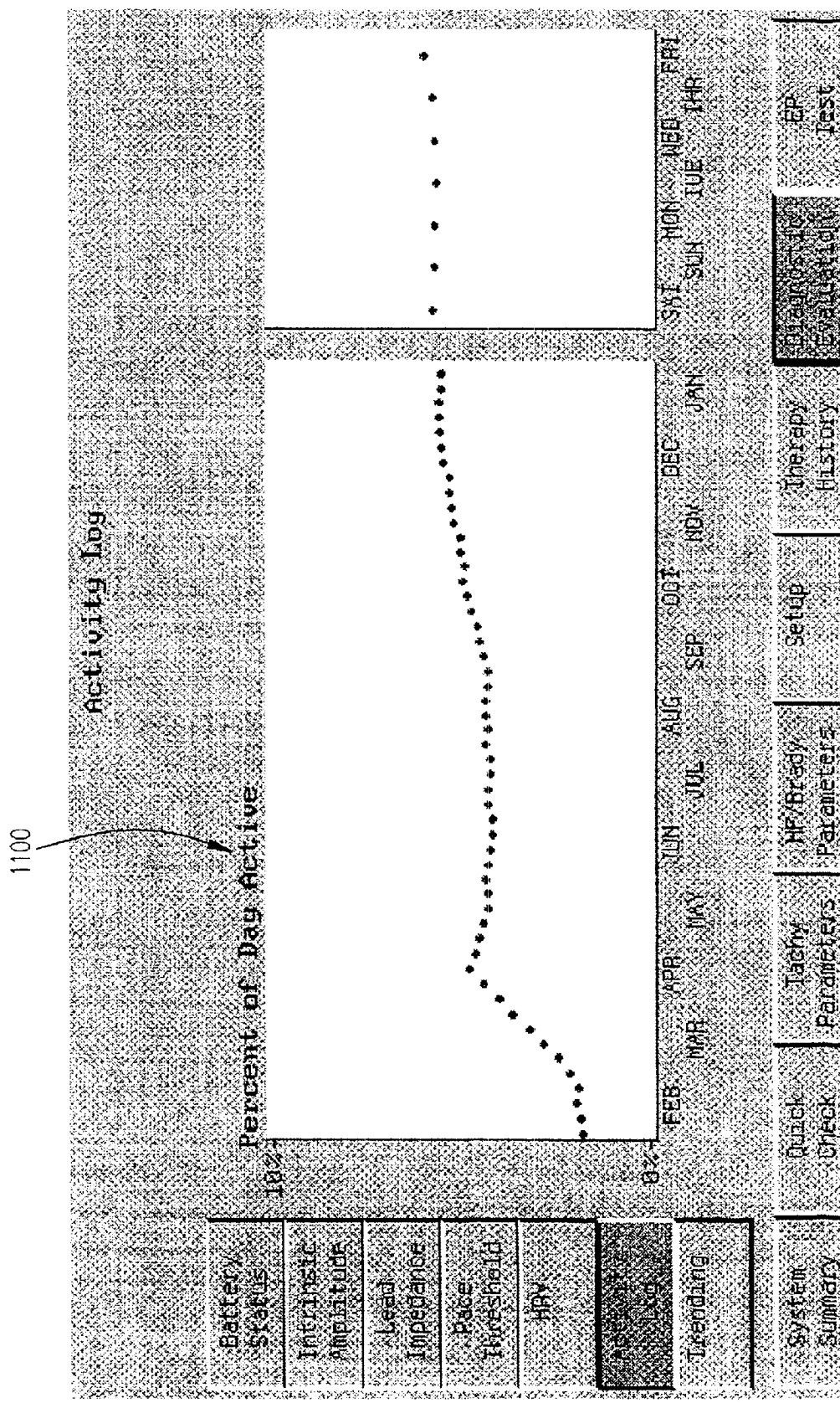
FIG. 11 is a display of an activity log recorded by a CRM device.

FIGS. 9–11 show displays of various types of data associated with a patient and the CRM device. The displays are produced by programmer 60, for example on screen 102, or by a display device that interacts with the programmer 60.

FIG. 9 shows two graphs 910, 920 of the same type of data, namely, heart rate variability, but the data shown on the graphs was recorded under distinct conditions, namely, two different periods of time. The conditions 915, 925 at which each set of heart rate variability data was recorded is displayed adjacent each graph. This type of dual graph visually informs the physician of changes in the same type of data and the change in the conditions at which such data was recorded. Conditions at which the data was recorded include a set of parameters that are related to the data displayed in graphs 910, 920.

In the illustrated FIG. 9 embodiment, the top display is the last measured heart rate variability graph 910 and condition data 915, both recorded on a certain date and the lower display is a reference heart rate variability graph 920 and condition data 925, both recorded on a previous date. Each condition data display 915, 925 includes a title, here "last measured" and "reference" respectively, the date and time of data measurement, and data representing measured data and programmed parameters. The illustrated embodiment shows data that includes measured and/or calculated data such as the footprint of the accompanying graph (a measure of the non-white space in the graph), which is the percent of time heart rate variability data was gathered during the recording period, and SDANN (standard deviation of the means of all the successive 5 minutes segments contained in a whole recording). The illustrated embodiment shows data that includes programmed parameters such as pacemaker mode, the lower rate limit, the maximum tracking rate, the atrio-ventricular delay, and the pacing chamber. The physician can visually recognize differences in the patient's heart rate variability and the changes in conditions at which the heart rate variability was acquired based on the simultaneous display of the two heart rate variability graphs 910, 920 along with the associated data 915, 925 for each graph. This allows the physician to accurately interpret the displayed data in context with associated data and/or programmed parameters.

FIG. 10 shows graphs 1010, 1020, 1030 of trend data for three different measured data sets, namely heart rate, footprint, and SDANN. Trend data is the value of a select measurement over a period of time. In the illustrated embodiment the each graph 1010, 1020, 1030 includes two sub-graphs. The first sub-graph displays the data in weekly increments. The second sub-graph displays the data according to the day of the week it was measured. The three displays and sub-graphs share the same X-axis time line and are simultaneously displayed so that a physician can easily see correlations, if any, between the displayed trend graphs. This allows the physician to accurately interpret the displayed, measured data in context with other displayed, measured data and helps provide a more accurate diagnosis.

FIG. 11 shows a further graph 1100 having the same sub-graph layout and X-axis time line as in FIG. 10. Graph 1100 displays the percent of time that a patient is active, sometimes measured by the CRM device 20 as the time when the patient's activity, as determined by cardiac data, is above a certain threshold value. Graph 1100 simultaneously displays two interpretations of the activity measurements. The first sub-graph, shown on the left in FIG. 11, displays activity data over the course of a year in weekly increments. The second sub-graph, shown on the right in FIG. 11 shows the activity data as a function of the day of the week it was measured. Thus, the physician can visually determine the patient's activity level and provide a diagnosis based on display 1100.

It will be recognized that it is within the scope of the present invention to select the data and/or parameters simultaneously displayed so that the display will be of most use to a physician when interpreting the displayed data. For example, the activity data display 1100 could be selected to display with the heart rate trend display 1010. Such a selection of data displays provides the physician with a tool which assists in quick and accurate interpretation of the data measured by CRM device 20 and parameters programmed into CRM device 20. Thus, the display of data and/or parameters according to the present invention includes simultaneously displaying measured data with other measured data, measured data with programmable parameters, and programmable parameters with other programmable parameters. Moreover, the measured data includes both synchronous data, periodic data, and asynchronous data. It will be appreciated that various combinations of data types and parameters can be simultaneously displayed.

While many of the embodiments described herein and shown in the drawings display data in a specific format, it will be understood that other formats are within the scope of the present invention. Such other formats include changing the display color, if a color display is available, or changing the grey-scale, if only a monochrome display is available, for first data before and after an event or in the presence of second data correlated to the first data. Other formats further include different cross-hatching and different line types. Nevertheless, each of the data formats provides the viewer with visual indication of a change in data or a change in the environment in which the data was recorded.

Although the invention has been described in conjunction with the foregoing specific embodiments, many alternatives, variations, and modifications will be apparent to those of ordinary skill in the art. Such alternatives, variations, and modifications are intended to fall within the scope of the following appended claims. For example, the CRM system controls a large number of programmable parameters of the CRM device and stores a large number of CRM device performance data sets and sensed patient health data. It will be understood that the above described embodiments are examples and numerous correlations of data, data and parameter, etc. are within the scope of the present invention.

What is claimed is:

1. A cardiac rhythm management system comprising a cardiac rhythm management (CRM) device and a data correlation device, said CRM device including programmable parameters controlling operation of said CRM device;

said data correlation device being adapted to receive data from said cardiac rhythm management device, said data correlation device including a memory, a processor and an output unit for displaying data, said memory storing a first data set and a second data set, said first data set being a type distinct from said second data set, said second data set including a type and a time of setting the programmable parameter, said processor correlating said first data set and said second data set and sending said correlated first and second data sets to said output unit, said first and second data sets being simultaneously displayed by said output unit.

2. The system according to claim 1, wherein said first data set is periodically collected data and said second data set is asynchronous data.

3. The system according to claim 1, wherein at least one of said CRM device parameter includes an accelerometer response factor, said first data set is patient activity data, and said second data set includes the time at which said accelerometer response factor was changed.

4. The system according to claim 1, wherein at least one of said CRM device parameter includes ventricular sensitivity, said first data set is a number of shocks in a given time period, and said second data set includes a time at which said ventricular sensitivity was changed.

5. The system according to claim 1, wherein said first data set includes patient health data, said second data set including a type and a time of therapy administered by said cardiac rhythm management system.

6. The system according to claim 5, wherein said first data set includes patient activity data and pacing chamber data.

7. The system according to claim 1, wherein said data correlation device is a programmer which is adapted to send programming instructions to said cardiac rhythm management device.

8. A cardiac rhythm management system including a cardiac rhythm management device and a data correlation unit, said data correlation unit being adapted to receive data from said cardiac rhythm management device and comprising a memory for storing data, a processor for correlating data and an output unit for displaying data, said memory containing a first data and a second data, said first data and said second data being a same type data, said processor correlating said first data and said second data and sending said correlated first and second data to said output unit, said first and second data being simultaneously displayed on said output unit;

wherein said first data is displayed with a third data representing a context in which said first data was collected, and said second data is displayed with a fourth data representing a context in which said second data was collected.

9. The system according to claim 8, wherein said first data is heart rate variability data, said third data includes a time at which said first data was collected, and said fourth data includes a time at which said second data was collected.

10. The system according to claim 8, wherein said third and fourth data include the same type of data.

11. The system according to claim 10, wherein said third and fourth data include at least one of CRM device pacing mode, pacing chamber, lower pacing limit, maximum tracking rate, and atrial-ventricular delay.

12. A system for displaying cardiac data from a cardiac rhythm management device, comprising:

a memory containing a first data set and a second data set, said first data set being distinct from said second data set, said second data set including a type and a time of setting a programmable parameter of the cardiac rhythm management device;

a processor connected to said memory, said processor correlating said first data set and said second data set;

an output unit connected to said processor, said output unit receiving said correlated first and second data sets from said processor, said first and second data sets being simultaneously displayed on said output unit.

13. The system according to claim 12, wherein said first data set is periodically collected data from the cardiac rhythm management device and said second data set is asynchronous data.

14. The system according to claim 13, wherein said first data set is patient activity data, and said second data set includes said time of setting at which an accelerometer response factor of the cardiac rhythm management device was changed.

15. The system according to claim 14, wherein said first data set is a number of shocks in a given time period, and said second data set includes said time of setting at which a ventricular sensitivity of the cardiac rhythm management device was changed.

16. The system according to claim 12, wherein the first and second data sets are displayed over a same time period.

17. A system for displaying cardiac data from a cardiac rhythm management device, comprising:

a memory containing a first data set and a second data set, said first data set being distinct from said second data set, first data set including heart rate data, said second data set is one of a footprint of a heart rate variability graph and SDANN;

a processor connected to said memory, said processor correlating said first data set and said second data set;

an output unit connected to said processor, said output unit receiving said correlated first and second data sets from said processor, said first and second data sets being simultaneously displayed on said output unit.

18. A method of displaying cardiac health related data, comprising:

acquiring a cardiac health related data set;

programming a programmable parameter of a cardiac rhythm management device;

storing a time at which the programmable parameter was programmed;

correlating the data set with the stored time at which the programmable parameter was programmed; and outputting the correlated data set and stored time on a single display.

19. The method according to claim 18, wherein acquiring the data set includes acquiring data before and after the stored time such that the effect of the programmed parameter had on the data in the data set is visually displayed.

20. The method according to claim 18, wherein acquiring the data set includes downloading the data set from an implanted cardiac rhythm management device.

21. The method according to claim 18, wherein correlating the data set and the stored time includes graphing the data set versus time and overlaying the stored time on a same graph.

22. The method according to claim 21, wherein outputting the correlated data set and stored time includes assigning the data set and stored time visually different elements on the graph.

23. The method according to claim 18, wherein acquiring the data set includes recording a number of shocks by the cardiac rhythm management device in predetermined time periods; and correlating the data set and the stored time includes graphing the number of shocks in select time periods versus time and including an indicator of the time at which the parameter change occurred on the same graph.

24. The method according to claim 23, wherein storing the time at which the operational parameter was changed includes recording the time at which ventricular sensitivity of the cardiac rhythm management device occurred.

25. The method according to claim 18, wherein acquiring the data set includes recording patient activity, and storing the time at which the operational parameter was programmed includes a time at which an accelerometer response factor of the cardiac rhythm management device was changed.

26. The method according to claim 18, wherein acquiring the data set includes measuring patient activity with the cardiac rhythm management device as a percentage of time that a patient's activity level is above a given threshold value.

\* \* \* \* \*

UNITED STATES PATENT AND TRADEMARK OFFICE
CERTIFICATE OF CORRECTION

PATENT NO. : 6,665,558 B2
DATED : December 16, 2003
INVENTOR(S) : Kalgren et al.

It is certified that error appears in the above-identified patent and that said Letters Patent is hereby corrected as shown below:

<u>Title page,</u>
Item [75], Inventors, delete "White Bear Lake, MN" and insert -- Overijse, Belgium --, therefor.

Signed and Sealed this

Sixteenth Day of March, 2004

JON W. DUDAS
*Acting Director of the United States Patent and Trademark Office*